(12) United States Patent
Spanier

(10) Patent No.: US 9,555,173 B2
(45) Date of Patent: Jan. 31, 2017

(54) PULSATILE BLOOD PUMP

(71) Applicant: ABIOMED EUROPE GmbH, Aachen (DE)

(72) Inventor: Gerd Spanier, Aachen (DE)

(73) Assignee: ABIOMED EUROPE GMBH, Aachen (DE)

( * ) Notice: Subject to any disclaimer, the term of this patent is extended or adjusted under 35 U.S.C. 154(b) by 0 days.

(21) Appl. No.: 14/396,718

(22) PCT Filed: Apr. 25, 2013

(86) PCT No.: PCT/EP2013/058648
§ 371 (c)(1),
(2) Date: Oct. 23, 2014

(87) PCT Pub. No.: WO2013/160411
PCT Pub. Date: Oct. 31, 2013

(65) Prior Publication Data
US 2015/0133722 A1    May 14, 2015

(30) Foreign Application Priority Data

Apr. 27, 2012    (DE) .......................... 10-2012-207042

(51) Int. Cl.
*A61M 1/10*    (2006.01)
*A61M 1/12*    (2006.01)

(52) U.S. Cl.
CPC ......... *A61M 1/1005* (2014.02); *A61M 1/1044* (2014.02); *A61M 1/1081* (2013.01);
(Continued)

(58) Field of Classification Search
CPC .. A61M 1/1086; A61M 1/125; A61M 1/1044; A61M 1/1005; A61M 1/122
See application file for complete search history.

(56) References Cited

U.S. PATENT DOCUMENTS

| 5,314,469 A | 5/1994 | Gao |
| 2005/0096496 A1 | 5/2005 | Spence |

(Continued)

FOREIGN PATENT DOCUMENTS

| DE | 102006035548 A1 | 1/2008 |
| DE | 102010018233 A1 | 10/2011 |

(Continued)

*Primary Examiner* — Joseph Dietrich
(74) *Attorney, Agent, or Firm* — Ropes & Gray LLP

(57) ABSTRACT

An extravascular pulsation blood pump possesses a bidirectionally acting pumping system (P, M) having a pump (P) which is connected via a first conduit ($L_1$) to the left ventricle (LV) and via a second conduit ($L_2$) to the aorta (AO). By means of a control means (St), the pump (P) is operated alternately in one and the other direction according to a given cardiac rhythm, so that alternately blood is sucked through the first conduit ($L_1$) and simultaneously blood ejected through the second conduit ($L_2$) to the same extent, on the one hand, and blood is sucked through the second conduit ($L_2$) and simultaneously blood ejected through the first conduit ($L_1$), on the other hand. The pulsation blood pump combines the functions and advantages of an extravascular copulsation pump with those of an extravascular counterpulsation blood pump.

15 Claims, 4 Drawing Sheets

Figure 1:
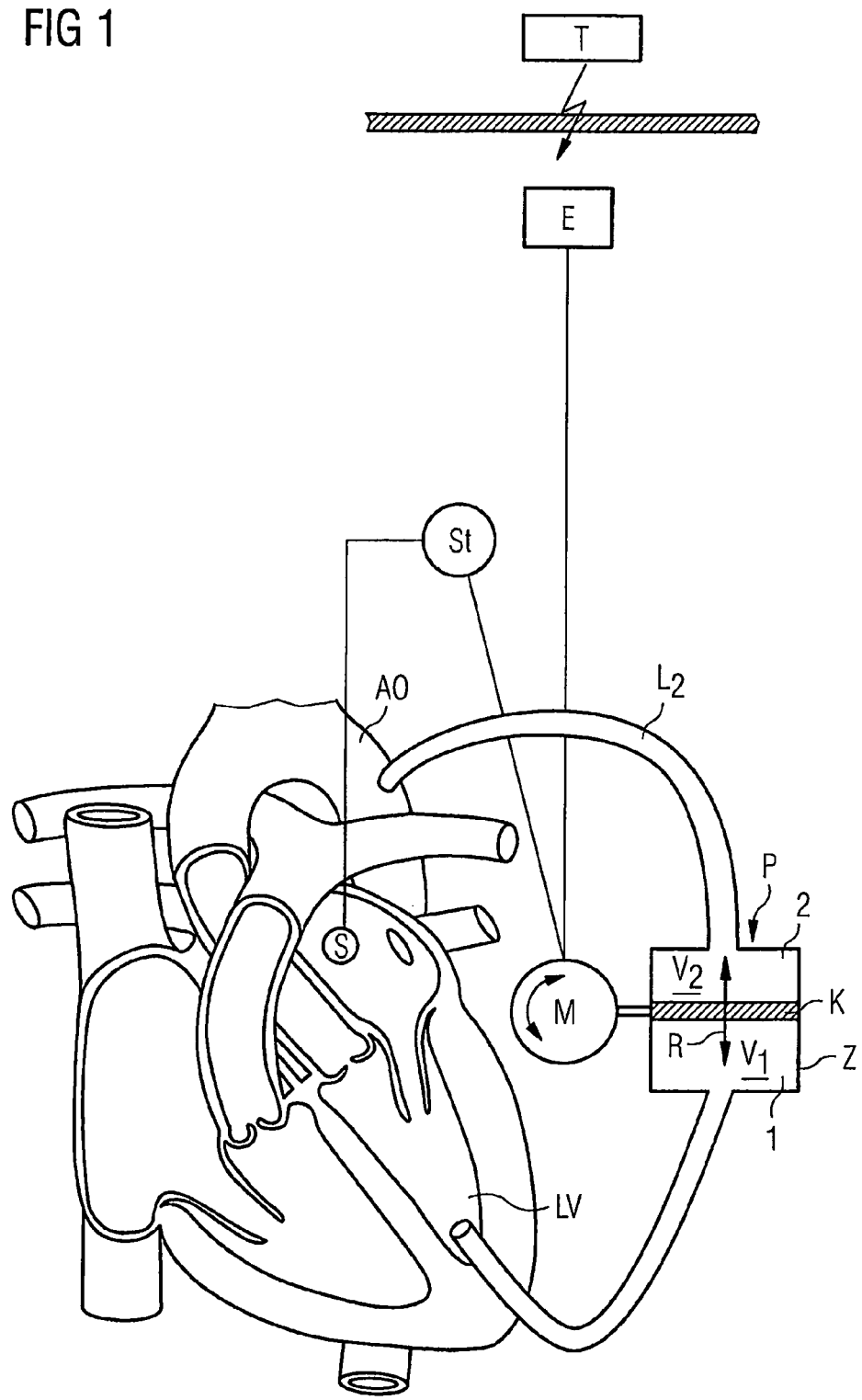

(52) U.S. Cl.
CPC .......... *A61M 1/1086* (2013.01); *A61M 1/122* (2014.02); *A61M 2230/04* (2013.01)

(56) References Cited

U.S. PATENT DOCUMENTS

| | | |
|---|---|---|
| 2010/0036486 A1 | 2/2010 | Mazur |
| 2010/0082099 A1 | 4/2010 | Vodermayer |
| 2010/0268333 A1* | 10/2010 | Gohean .................. F04B 35/04 623/3.14 |
| 2011/0015732 A1* | 1/2011 | Kanebako ........... A61M 1/1086 623/3.1 |
| 2013/0218268 A1 | 8/2013 | Schmid |

FOREIGN PATENT DOCUMENTS

| | | |
|---|---|---|
| EP | 2388028 A1 | 11/2011 |
| WO | WO-2004/078025 A2 | 9/2004 |
| WO | WO-2007/089500 A2 | 8/2007 |

* cited by examiner

PULSATILE BLOOD PUMP

RELATED APPLICATIONS

This application is the U.S. National Stage of International Application Number PCT/EP2013/058648, filed Apr. 25, 2013, which claims priority to German Patent Application No. 10 2012 207 042.7, filed Apr. 27, 2012. The entire contents of the foregoing applications are hereby incorporated herein by reference.

This invention relates to an extravascular pulsation blood pump and finds application in supporting the pulsation of the human heart.

To enable a previously damaged human heart to recover, the pulsation of the heart is supported by means of artificial pumps. So-called intraaortic balloon pumps (IABPs) find wide application. A balloon is thus placed in the aorta and filled with helium and emptied alternately, according to the cardiac rhythm, through a relatively long catheter from outside the body. Emptying is effected shortly before the onset of systole to thereby significantly lower the blood pressure in the aorta, so that the heart can eject its blood volume into the aorta against a low aortic pressure. At the onset of diastole the balloon is filled again, thereby increasing the pressure in the aorta and thus driving the blood into the organs and peripheral blood vessels. This method is also known as the counterpulsation or aortic counterpulsation method.

US 2005/0096496 A1 points out various disadvantages of intraaortic balloon pumps. Among other things, they involve the risk of infection due to the indwelling catheter, and do not allow the patient to get out of bed. Hence, they are normally only used for one or two days, although chronically weak hearts actually require long-term support. Moreover, the catheter hinders blood flow in the blood vessel. Hence, it is proposed therein to connect a subcutaneously implanted pump to an arterial blood vessel via a conduit and to suck blood out of the artery when the heart contracts (systole) and pump it back into the artery again when the heart relaxes (diastole). In this manner a counterpulsation is obtained without a balloon closing the blood vessel itself or a catheter extending within the blood vessel. The pump can be configured as a bladder, sack or diaphragm pump. It is also proposed to supplement the extravascular counterpulsation pump by a second extravascular pump with which blood is continuously sucked directly out of the heart via a first conduit and fed via a second conduit directly to that artery to which the extravascular counterpulsation pump is also connected.

Extravascular counterpulsation blood pumps can attain substantially higher volume flows than conventional aortic balloon pumps, namely up to 2.4 l per minute instead of 0.7 l per minute. Such counterpulsation systems can furthermore be replaced or supplemented by copulsation systems in which the conduit of the extravascular blood pump is connected directly to a ventricle of the heart. The pump then sucks blood out of the ventricle into a chamber temporarily during diastole to thereby minimize the blood volume in the ventricle and prevent a dilatation of the heart, and pumps this blood during the following systole back into the ventricle, from where it flows into the arterial blood vessel through the open cardiac valve.

Both counterpulsation and copulsation by means of an extravascular blood pump fully implanted in the body involve the problem that the blood sucked by means of the pump must be stored temporarily in a reservoir. For this purpose, the blood pump possesses a so-called compliance chamber whose volume accordingly decreases upon filling of the blood pump. Compliance chambers are relatively voluminous. This applies in particular to gas-filled compliance chambers, because in the case of a small gas-filled compliance chamber the pump would require a great deal of energy to accordingly compress the gas volume of the compliance chamber during the suction phase. This problem doubles when both a counterpulsation pump and a copulsation pump are implanted simultaneously.

The object of the present invention is to improve the support of the heart's pulsation by means of extravascular pulsation blood pumps, and in particular to propose a pulsation blood pump that is optimized with respect to its functionality and overall size in comparison to the previously described extravascular pulsation blood pump.

This object is achieved by a pulsation blood pump having the features of claim 1. Claims dependent thereon state advantageous embodiments and developments of the invention.

The pulsation blood pump according to the invention combines the functions of counterpulsation and copulsation and possesses for this purpose a bidirectionally acting pumping system which is connected via two conduits to a blood vessel, for example the aorta, on the one hand, and to a heart chamber, for example the left ventricle, on the other hand. Between the heart and the blood vessel there is a valve, which is normally formed by a cardiac valve. The bidirectional pumping system is arranged for removing a first quantity of blood from the heart during diastole of the heart and substantially simultaneously bringing a second quantity of blood into the blood vessel. On the other hand, the pumping system is arranged for removing a quantity of blood corresponding to the second quantity from the blood vessel again during the heart's systole following the diastole and substantially simultaneously in turn bringing a quantity of blood corresponding to the first quantity into the heart. The first and second quantities can be identical, but this is not necessary, for the pumping system can be configured as a differential pumping system.

As a result, the heart is considerably relieved both during systole and during diastole. For the heart pumps against a lower arterial pressure during systole because blood is simultaneously being removed from the blood vessel into which the heart is pumping. During the subsequent diastole the heart is relieved by a part of the filling volume being removed from the relevant heart chamber by means of the blood pump and brought into the heart chamber again only during the following systole. The heart chamber thus expands less, thereby preventing or reducing a dilatation or widening of the heart chamber. Even when the heart chamber widens to its normal extent and fills with blood during diastole, it is at least achieved by means of the pulsation blood pump according to the invention that the filling volume of the relevant heart chamber "increases" by the quantity of blood removed from the heart chamber by means of the bidirectional pumping system, because this very quantity is returned to the heart chamber again during the following systole and this quantity of blood is ejected into the connected vascular system at the same time as the heart activity. While the heart is relieved and/or extended in capacity during diastole in this manner, the pressure in the appurtenant blood vessel, for example the aorta, is increased due to the blood quantity simultaneously brought into the blood vessel, so that the organs and adjacent blood vessels are supplied with more blood due to the increased blood pressure in the relevant blood vessel. The pulsation blood pump according to the invention having a bidirectionally acting pumping system thus combines the functions and advantages of a copulsating extravascular blood pump with those of a counterpulsating extravascular blood pump.

A substantial further advantage of the pulsation blood pump according to the invention, however, is that it is not necessary to provide a separate compliance chamber for each of these two functions. Instead, the pumping system can have for example a first pumping chamber with variable volume which is attached for example to the heart chamber, and a second pumping chamber with variable volume which is then attached to the corresponding blood vessel, the two pumping chambers being so coupled with each other that to the same extent as blood is sucked into the first pumping chamber, blood is ejected from the second pumping chamber, and vice versa. Accordingly, the two pumping chambers respectively act as a compliance chamber for the other pumping chamber. This can be illustrated by comparison with a double-acting cylinder piston. While displacement of the piston within a cylinder reduces the volume before the piston in the moving direction, it increases the volume behind the piston. The decreasing volume before the piston is comparable to a compliance chamber for the increasing volume behind the piston. In the reverse moving direction of the piston this functionality is accordingly reversed. That is to say, the pressurized chamber of the piston cylinder always acts simultaneously as a pumping chamber out of which something is pumped, and as a compliance chamber for the chamber located on the other side of the piston.

This basic principle can be modified in different ways. In particular, there can be realized by means of a differential piston a differential pumping system which pumps different volume flows in one and the other direction, the piston stroke being identical in absolute terms.

According to the invention, the respective pressures on the suction side of the pump help to minimize the required energy for displacing the piston or the hydraulic liquid. This is crucial in particular for a fully implantable system in order to minimize battery size.

Another modification of the above-described basic principle provides for separate compliance chambers. That is to say, while the volume on one side of the piston acts as a pumping chamber and as a compliance chamber simultaneously with the above-described double-acting cylinder piston, these two functions are mutually separate in this modified embodiment. Thus, the bidirectional pumping system can possess a first pumping chamber with variable volume and a first compliance chamber with variable volume which together form a first double chamber, and a second pumping chamber with variable volume can form together with a second compliance chamber with variable volume a second double chamber. The compliance chambers are separated from the respective appurtenant pumping chamber here by a variable partition, which can be configured for example as a flexible membrane or at least comprise a flexible membrane. By means of a pump a fluid is now pumped back and forth between the two compliance chambers, so that, depending on the pumping direction, blood is ejected from the one appurtenant pumping chamber while blood is simultaneously sucked into the other appurtenant pumping chamber, and vice versa.

The advantage of this last-mentioned modification of the basic principle over conventional systems is primarily that the compliance chambers can be filled with a liquid instead of a gas, so that the compliance chambers do not have to be greater than the blood volume to be received by the pumping chambers. This makes the system especially efficient and furthermore safer in comparison to gas-filled compliance chambers. The liquid to be used may be any liquid. A further advantage of this modification over the double-acting cylinder piston is that the pump is decoupled from the blood, that is to say, the pump only pumps liquid between the two compliance chambers, and not blood.

The pulsation blood pump according to the invention can be implanted completely into a patient's body. But at least the pumping system is provided and arranged for being implanted. An energy supply means for the pump or, if the pump is driven by means of a separate motor, for this motor, can likewise be implantable and be charged from time to time or continuously for example transcutaneously either using physical contacts or preferably contactlessly.

The pulsation blood pump according to the invention of course comprises a control means which is provided and arranged for operating the bidirectional pumping system alternately in one and the other direction according to a given cardiac rhythm. The cardiac rhythm can be captured in different ways using suitable sensor means, and the thus established cardiac rhythm data transmitted to the control means. In particular, the pulsation blood pump can be controlled by means of the same cardiac rhythm data that are also employed for controlling conventional synchronous heart-support systems, such as e.g. intraaortic blood pumps.

Figure 2:
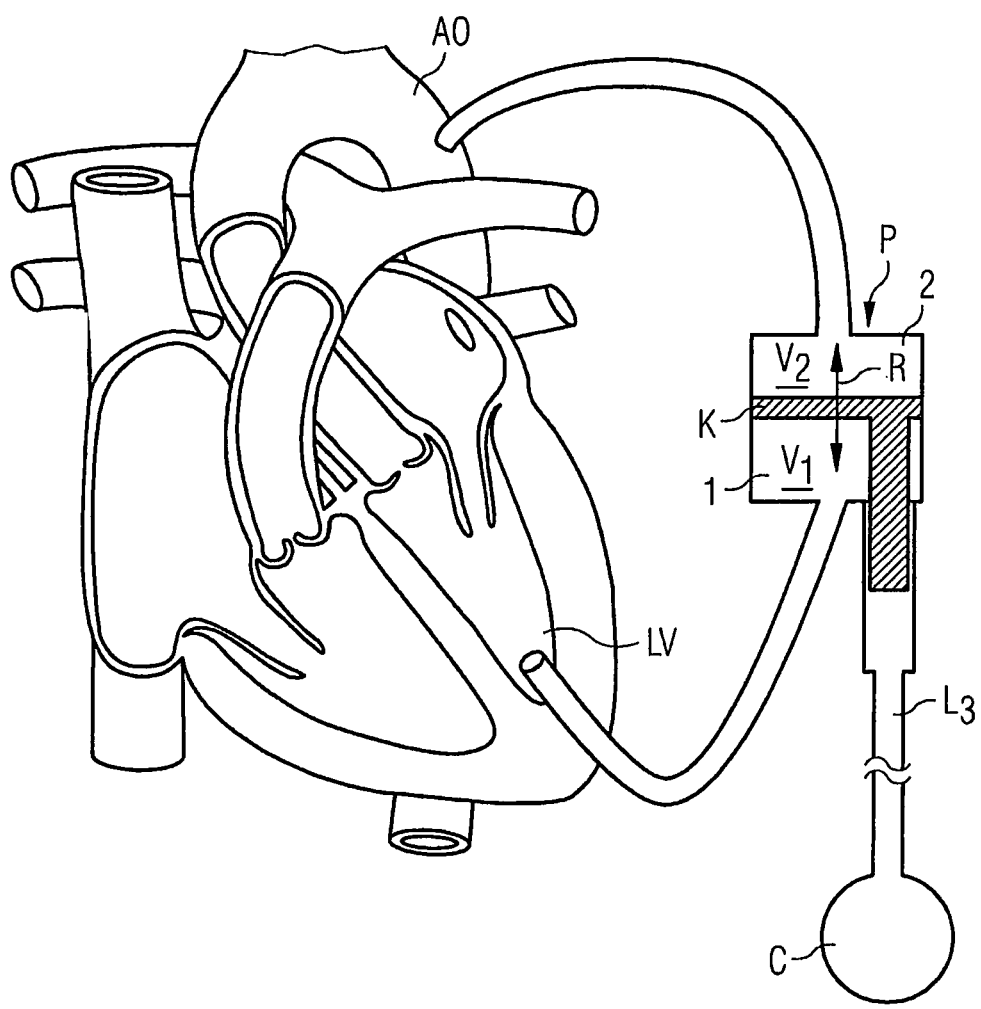
Figure 3:
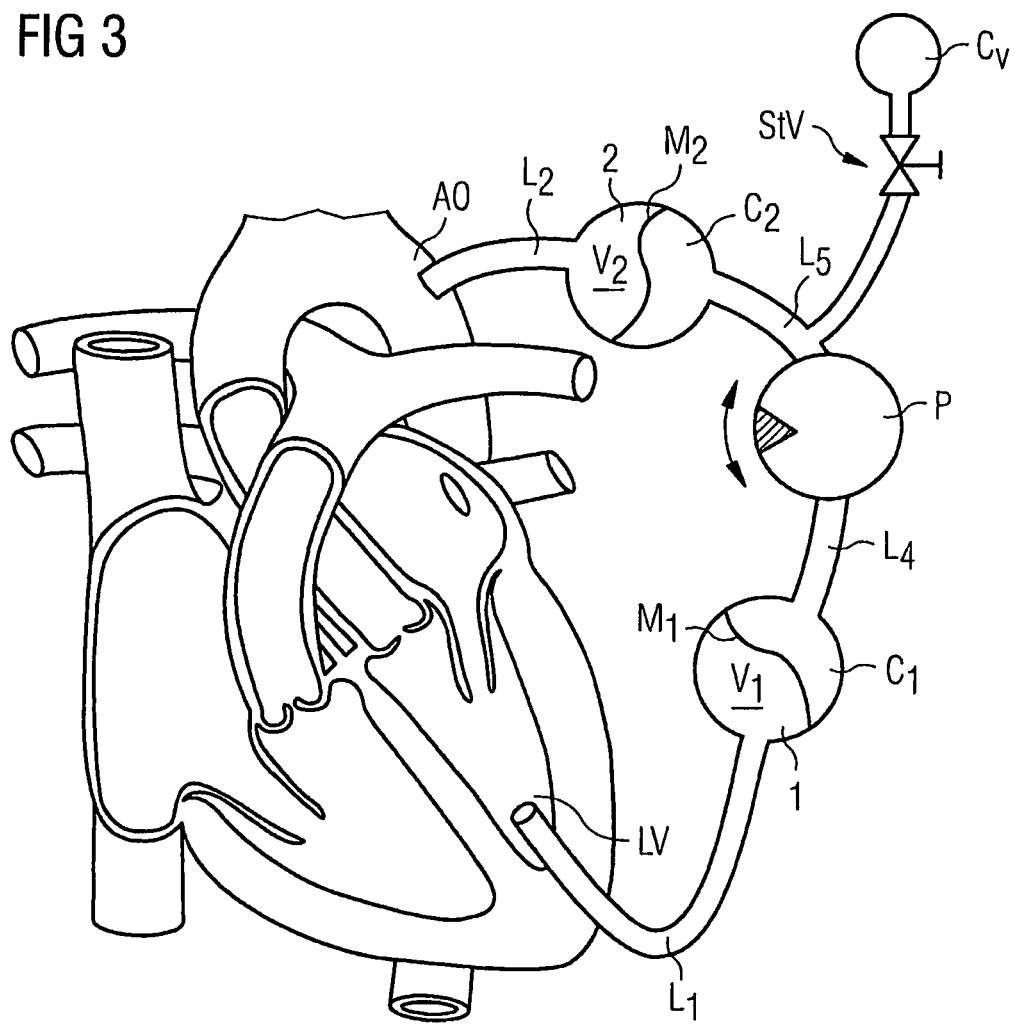
Figure 4:
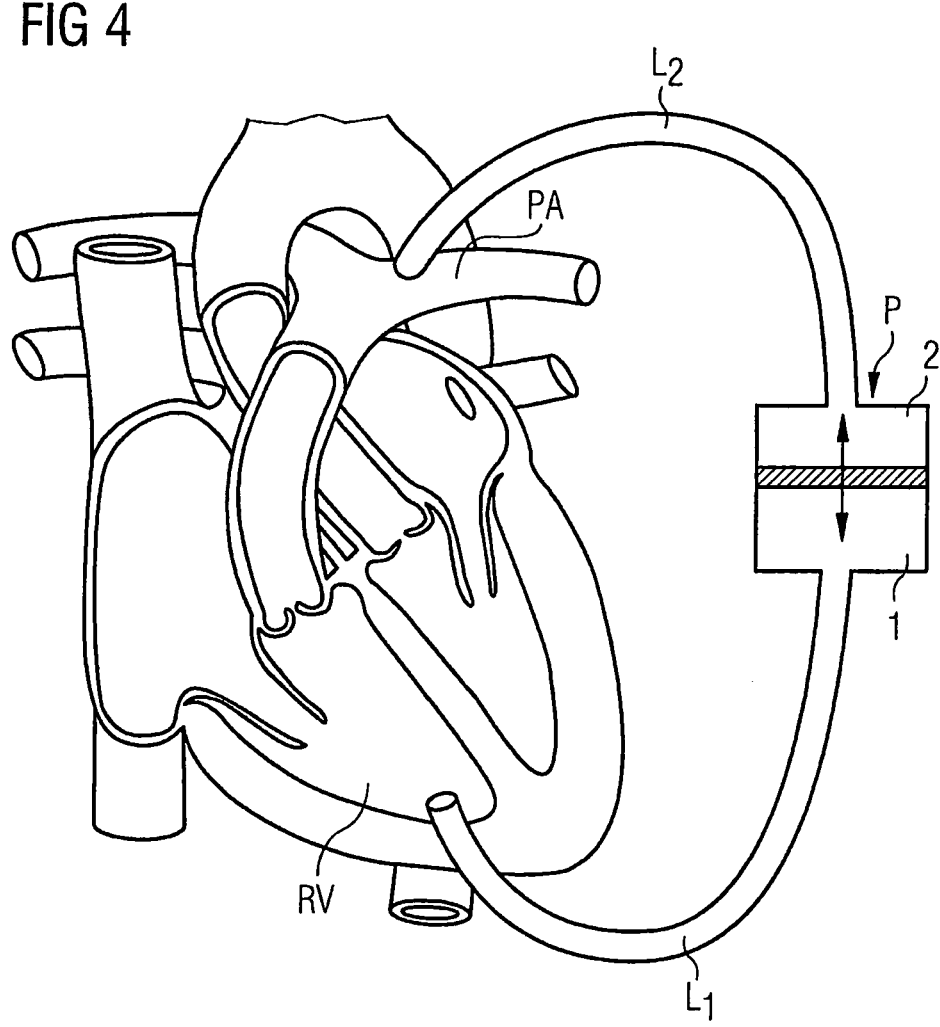

Hereinafter the invention will be explained by way of example with reference to the accompanying drawings. Therein are shown:

FIG. 1 the basic principle of a pulsation blood pump according to the invention by the example of support for the left ventricle, FIG. 2 a first modification of the basic principle, FIG. 3 a second modification of the basic principle, and FIG. 4 the basic principle by the example of supporting the right ventricle.

With reference to the schematic representation according to FIG. 1, the basic principle of the pulsation blood pump according to the invention will be explained hereinafter. The pulsation blood pump consists substantially of a bidirectional pumping system which is connected via a first conduit $L_1$ and a second conduit $L_2$ to a blood vessel, here the aorta AO, on the one hand, and to a heart chamber, here the left ventricle LV, on the other hand. The bidirectional pumping system consists substantially of a pump P and a motor M driving the pump P. How the pump and/or the motor are concretely constituted and coupled with each other in the particular case is of minor importance to the invention. What is essential to the basic principle represented in FIG. 1 is that the pump P is configured in the manner of a double-acting piston-cylinder arrangement wherein the piston K is moved in a direction back and forth within a cylinder Z. This changes the volumes $V_1$ and $V_2$ in the mutually opposing pumping chambers 1 and 2 separated by the piston K.

The motor M and thus the pump P is operated alternately in one and the other direction according to a given cardiac rhythm via a control means St. The cardiac rhythm data for controlling the pumping system (e.g. pressure, ECG, contraction, PPS, etc.) can be captured by means of a sensor means S coupled with the control means St and be transmitted to the control means St. This is indicated in FIG. 1 only schematically by a sensor S lying in the atrium of the left ventricle LV, which may be a pressure sensor.

The energy necessary for operating the pumping system can be made available from an energy storage device E, which is accordingly charged for example contactlessly either continually or preferably temporarily via a transmitter T.

Employing this energy and with consideration of the cardiac rhythm data processed by the control means St, the piston K is now displaced according to the cardiac rhythm such that during systole the volume $V_1$ of the pumping chamber 1 is reduced and blood is accordingly pumped out of the pumping chamber 1 via the conduit $L_1$ into the left ventricle LV. Thus, blood is simultaneously sucked out of the aorta AO through the conduit $L_2$ into the increasing volume $V_2$ of the second pumping chamber 2. The left ventricle LV thus works against a reduced aortic pressure, and also the blood volume displaced out of the pumping chamber 1 flows through the left ventricle LV and the aortic valve into the aorta AO. During the following diastole the piston K is moved in the opposite direction, so that blood is sucked out of the left ventricle LV through the conduit $L_1$ into the pumping chamber 1, and simultaneously a corresponding quantity of blood is pumped out of the second pumping chamber 2 through the conduit $L_2$ into the aorta AO. This minimizes the expansion of the left ventricle LV and counteracts a dilatation of the heart, so that the heart can recover. Simultaneously, the blood pumped into the aorta AO so increases the blood pressure in the aorta AO that the blood flows reliably into the organs, i.e. also in the heart, and the peripheral blood vessels. Reduction of the diastolic ventricular size enables the wall stress of the myocardium to be minimized and thus the heart to be supplied with blood more efficiently.

FIG. 2 shows a first modification of this basic principle. The piston K is configured here as a differential piston with two piston areas of different size. Accordingly, the volumes $V_1$ and $V_2$ do not change to the same extent upon a motion of the piston K in the direction R. In the concretely represented exemplary embodiment, a smaller quantity of blood is pumped back and forth between the left ventricle LV and the pumping chamber 1 due to the differential piston K than between the aorta AO and the second pumping chamber 2. Depending on which heart function is to be mainly supported by the pulsation blood pump, the greater piston area of the differential piston can lie on the side of either the heart or the blood vessel. However, the differential piston K requires on the side of the smaller piston area an additional compliance chamber C, which is connected to the pump P via a conduit $L_3$. The compliance chamber C takes up the difference resulting from the volume displacement $V_2$ and $V_1$, which is positive or negative depending on the displacement direction of the differential piston K. The compliance chamber C is placed at a location within the patient where it is only subjected to low ambient pressure, for example in the abdomen, and is connected to the pump P via a conduit $L_3$. In the conduit $L_3$ and the compliance chamber C there is preferably located a liquid, i.e. in particular no blood.

FIG. 3 shows a second modification of the basic principle. Here, the first pumping chamber 1 forms with a first compliance chamber $C_1$ a first double chamber, and the second pumping chamber 2 with a second compliance chamber $C_2$ a second double chamber. The pumping chambers 1 and 2 are separated from the compliance chambers $C_1$ and $C_2$ by a respective membrane $M_1$ and $M_2$, so that the volume $V_1$ and $V_2$ of the pumping chambers 1 and 2 is respectively variable. By means of a pump P, which is rendered here only schematically and may be a bidirectional rotation pump by way of example, a fluid is then pumped back and forth between the compliance chambers $C_1$ and $C_2$ according to the cardiac rhythm such that the variable volumes $V_1$ and $V_2$ of the two pumping chambers 1 and 2 change in the manner described hereinabove with reference to FIG. 1. For this purpose, the pump P is connected to the compliance chambers $C_1$ and $C_2$ via the conduits $L_4$ and $L_5$. In the conduits $L_4$, $L_5$ and the compliance chambers $C_1$, $C_2$ there is located a hydraulic fluid, i.e. in particular no blood. The pump P is thus reliably shielded from the blood circulation by means of the membranes $M_1$ and $M_2$. This is favorable for the structure and the effectiveness of the pumps P usable for the pumping system. Likewise, it considerably improves the fatigue strength of the pumping system.

An additional compliance chamber $C_V$ can be provided to take up volume fluctuations when the blood quantities $V_1$ and $V_2$ vary in size. FIG. 3 shows such an additional compliance chamber $C_V$ for taking up a part of the fluid pumped between the compliance chambers $C_1$ and $C_2$. This additional compliance chamber $C_V$ is optional and preferably adjustable variably with regard to its compliance properties. For adjusting the compliance properties, the control valve StV is used. The adjustment can be effected either prior to implantation or preferably for example by remote control also after implantation either as needed or continually. This enables the blood volumes received in the pumping chambers 1 and 2 to be varied, also dynamically, where applicable. A reason for such a measure may be for example that problems arise upon filling of one or the other of the two pumping chambers 1 and 2, or that the available volumes of the pumping chambers 1 and 2 are to be varied intentionally. Thus, it is possible that different volumes are pumped between the appurtenant compliance chambers $C_1$ and $C_2$ in spite of the common pump P for both pumping chambers 1 and 2, with the differential volume being taken up by the additional compliance chamber $C_V$. By means of the control valve StV it is thus possible to control the suction volumes and ejection volumes of the pumping chambers 1 and 2 variably. However, the volume reduction must not have the result that so much blood continually remains in one of the pumping chambers that successive agglutination of the blood is to be feared.

Instead of the additional compliance chamber $C_V$ being attaching to the conduit $L_5$, it can also be attached to the conduit $L_4$.

FIG. 4 finally shows yet a further modification of the basic principle represented in FIG. 1. Here, the conduits $L_1$ and $L_2$ of the pulsation blood pump are not connected to the left ventricle LV and the aorta AO, but instead to the right ventricle RV and the pulmonary arteries PA.

There is also the possibility to operate two separate pulsation blood pumps of the above-described type simultaneously for the left half of the heart, on the one hand, and for the right half of the heart, on the other hand.

The invention claimed is:

1. An extravascular pulsation blood pump, comprising
   a first conduit for connecting the pulsation blood pump to a heart chamber,
   a second conduit for connecting the pulsation blood pump to a blood vessel,
   a bidirectional pumping system which is arranged for alternately sucking blood through the first conduit and simultaneously ejecting blood through the second conduit, on the one hand, and sucking blood through the second conduit and simultaneously ejecting blood through the first conduit, on the other hand, and
   a control means which is provided for operating the pumping system alternately in one and the other direction according to a given cardiac rhythm.

2. The pulsation blood pump according to claim 1, comprising a sensor means coupled with the control means for capturing and transmitting cardiac rhythm data to the control means.

3. The pulsation blood pump according to claim 1, wherein the pumping system has a first pumping chamber with variable volume which is attached to the first conduit, and a second pumping chamber with variable volume which is attached to the second conduit, wherein the first and second pumping chambers are so coupled with each other that when blood is sucked into the first pumping chamber through the first conduit blood is ejected from the second pumping chamber into the second conduit, and vice versa.

4. The pulsation blood pump according to claim 3, wherein the first pumping chamber forms with a first compliance chamber with variable volume a first double chamber, and the second pumping chamber with a second compliance chamber with variable volume a second double chamber, wherein the first pumping chamber is separated from the first compliance chamber and the second pumping chamber from the second compliance chamber by a respective variable partition, and wherein the pumping system comprises a pump which is arranged for pumping a fluid back and forth between the first compliance chamber and the second compliance chamber.

5. The pulsation blood pump according to claim 4, wherein the partitions respectively comprise a flexible membrane.

6. The pulsation blood pump according to claim 4, wherein the fluid is a liquid.

7. The pulsation pump according to claim 1, wherein the pumping system is a differential pumping system.

8. The pulsation blood pump according to claim 1, wherein the pumping system is arranged for being implanted into a patient's body.

9. A method for supporting the pulsation of a heart, comprising the following steps:
   a) removing a first quantity of blood from the heart and bringing a second quantity of blood into a blood vessel substantially during a diastole of the heart,
   b) removing a quantity of blood corresponding to the second quantity from the blood vessel and bringing a quantity of blood corresponding to the first quantity into the heart substantially during a systole of the heart following the diastole, and
   c) repeating the steps a) and b) a plurality of times, characterized in that the first and second quantities of blood are removed and brought in by means of the same pumping system.

10. The method according to claim 9, wherein the blood removed from the heart and the blood vessel is stored temporarily in separate pumping chambers of the pumping system, and the same blood is brought into the heart or blood vessel again with the next systole or diastole.

11. The method according to claim 10, wherein the first pumping chamber is coupled with a first compliance chamber, and the second pumping chamber with a second compliance chamber, and wherein blood flow is effected from the first pumping chamber into the heart and from the second pumping chamber into the blood vessel by alternatingly filling and emptying the first and second compliance chambers.

12. The method according to claim 9, wherein the blood is removed from the heart from the left half of the heart, in particular the left ventricle, and the blood from the blood vessel from the aorta.

13. The method according to claim 9, wherein the blood is removed from the heart from the right half of the heart, in particular the right ventricle, and the blood from the blood vessel from the pulmonary arteries.

14. The method according to claim 9, wherein a greater quantity of blood is removed from the heart than from the blood vessel.

15. The method according to claim 9, wherein a greater quantity of blood is removed from the blood vessel than from the heart.

* * * * *